United States Patent
King et al.

(10) Patent No.: US 11,857,592 B2
(45) Date of Patent: Jan. 2, 2024

(54) ***POLYGALA* EXTRACT FOR THE TREATMENT OF ATTENTION-DEFICIT HYPERACTIVITY DISORDER**

(71) Applicant: BioLite, Inc., Taipei (TW)

(72) Inventors: Chi-Hsin Richard King, Taipei (TW); Hsien-Ming Wu, Taipei (TW); Howard Doong, Taipei (TW); Tsung-Shann Jiang, Taipei (TW)

(73) Assignee: BIOLITE, INC., Taipei (TW)

( * ) Notice: Subject to any disclaimer, the term of this patent is extended or adjusted under 35 U.S.C. 154(b) by 254 days.

(21) Appl. No.: 17/120,965

(22) Filed: Dec. 14, 2020

(65) Prior Publication Data
US 2022/0184167 A1 Jun. 16, 2022

(51) Int. Cl.
| | | |
|---|---|---|
| *A61K 36/69* | (2006.01) | |
| *A61K 47/02* | (2006.01) | |
| *A61K 47/12* | (2006.01) | |
| *A61K 9/48* | (2006.01) | |
| *A61P 25/28* | (2006.01) | |
| *A61K 9/00* | (2006.01) | |

(52) U.S. Cl.
CPC ............ *A61K 36/69* (2013.01); *A61K 9/0053* (2013.01); *A61K 9/485* (2013.01); *A61K 9/4825* (2013.01); *A61K 9/4858* (2013.01); *A61K 47/02* (2013.01); *A61K 47/12* (2013.01); *A61P 25/28* (2018.01); *A61K 2236/333* (2013.01)

(58) Field of Classification Search
CPC .... A61K 36/69; A61K 9/0053; A61K 9/4825; A61K 9/485; A61K 9/4858; A61K 47/02; A61K 47/12; A61K 2236/333; A61P 25/28
See application file for complete search history.

(56) References Cited

U.S. PATENT DOCUMENTS

| | | | | |
|---|---|---|---|---|
| 5,589,182 A * | 12/1996 | Tashiro | ................ | A61K 36/804 424/757 |
| 6,911,222 B2 * | 6/2005 | Ko | ......................... | A61K 36/69 424/773 |
| 7,507,424 B2 * | 3/2009 | Mitra | ................... | A61K 36/185 424/774 |

FOREIGN PATENT DOCUMENTS

| | | |
|---|---|---|
| CN | 104873687 A | 9/2015 |
| CN | 110314192 A | 10/2019 |
| KR | 20180119980 A | 11/2018 |

OTHER PUBLICATIONS

Bae, Medicines for ADHD, Hindawi, p. 1, June (Year: 2019).*
Lee, memory humans, Neurosci. Letters, p. 111, May (Year: 2009).*
Capelatto et al. "Cognitive Functions, Self-Esteem and Self-Concept of Children with Attention Deficit and Hyperactivity Disorder." Psicologia: Reflexao e Critica. vol. 27, Issue 2, ISSN 1678-7153. (2014), pp. 331-340, 10 pages.
Bryan DO, "Top 4 Supplement Additives You Should Know About" Dec. 1, 2018, 12 pages.

* cited by examiner

*Primary Examiner* — David J Blanchard
*Assistant Examiner* — Thurman Wheeler
(74) *Attorney, Agent, or Firm* — MUNCY GEISSLER OLDS & LOWE P.C.

(57) ABSTRACT

This invention relates to a method of treating Attention-Deficit Hyperactivity Disorder by orally administering to a subject a composition containing a Radix Polygalae (*Polygala tenuifolia* Willd) extract (such as PDC-1421). A solid dosage form of the composition can be prepared into the gelatin capsule. The oral administration of the composition in healthy volunteers was safe and well-tolerated for the daily dose from 380 mg to 3800 mg. The composition can be administered chronically over at least 25 days; the daily dose is administered once per day, twice per day, or three times per day, wherein each dose is 380-760 mg of the botanical extract.

4 Claims, 2 Drawing Sheets

POLYGALA EXTRACT FOR THE TREATMENT OF ATTENTION-DEFICIT HYPERACTIVITY DISORDER

BACKGROUND OF THE INVENTION

Technical Field of the Invention

This invention relates to a method for treating attention-deficit hyperactivity disorder (ADHD) by administering a composition comprising a Radix Polygalae (*Polygala temuifolia* Willd) extract. Particularly, the present invention relates to a method of orally administrating a composition comprising Radix Polygalae extract to a subject in need thereof for improving the performance of ADHD Rating Scale-Investigator Rated (ADHD-RS-IV) and/or the Conners' Adult Attention-Deficit/Hyperactivity Disorder Rating Scale-Self Report: Short Version (CAARS-S:S) and/or the Clinical Global Impression Scale (CGI).

Background

Attention-deficit/hyperactivity disorder (ADHD) has been recognized as an early-onset, common neuropsychiatric disorder with deficits in a wide-range of neuropsychological functions. Children with ADHD tend to have deficits in focused attention, cognitive and behavioral inhibition, sustained attention and vigilance. In adolescence and adulthood, hyperactivity diminishes, and inattention and impulsiveness become most impairing, especially in social situations. The percentage of children between 4 and 17 years of age diagnosed with ADHD was 11.0% (6.4 million) in 2011 (Visser, S. N. et al. J. Am. Acad. Child Adolesc. Psychiatry. 2014 January; 53(1):35-46). It is now clear that two thirds of children with ADHD will continue to have problems attributable to ADHD as adults.

Currently, there are two main classes of medications with proven efficacy for ADHD—stimulants and nonstimulants. Stimulants, such as amphetamines (AMPHs) and methylphenidates (MPHs), have been the mainstay of ADHD pharmacotherapy. However, approximately 30% of patients fail to respond to stimulant therapy. For patients with contraindications, or those who are adverse or nonresponsive to stimulants, nonstimulants, such a selective norepinephrine reuptake inhibitor (NRI) are alternative treatment options. Side effects of ADHD medications are generally mild, but conflicting data regarding risks of cardiovascular effects and adverse psychiatric effects have emerged over the past decade. Therefore, there is an unmet need for a new anti-ADHD medicine with higher efficacy and safety.

SUMMARY OF INVENTION

Accordingly, the present invention provides a method of treating attention-deficit/hyperactivity disorder (ADHD) comprising orally administering a composition comprising an effective amount of a botanical extract, wherein the botanical extract is one or a combination of: i) a polar solvent extract of Radix Polygalae (*Polygala tenuifolia* Willd), wherein the polar solvent is water or a mixture of water and methanol or ethanol; ii) an aqueous fraction resulting from an extraction of the polar solvent extract with an organic solvent; iii) an organic eluent obtained by introducing the polar solvent extract or the aqueous fraction into a reverse phase chromatography column, and eluting the column with water and an organic solvent; and iv) a filtrate of the organic eluent having a molecular mass less than 30,000 Dalton.

In some embodiments, the composition is administered in an oral dosage form with a daily dose of 380-3800 mg, comprising 380-760 mg of the botanical extraction.

In some embodiments, the daily dose is reached by administering the composition once per day, twice per day, or three times per day.

In some embodiments, the composition further comprises silicon dioxide and magnesium stearate.

In some embodiments, the composition is in a form of capsule, tablet, or film coated tablet.

In some embodiments, the composition is administered at the onset of an episode of a depressive disorder symptom.

In other embodiments, the composition is administered chronically.

In other embodiments, the composition is administered on a schedule throughout the day.

In some embodiments, the administration is daily for at least 25 days.

In some embodiments, the subject in need is under evaluation at the end of administration and after at least one month thereafter, wherein the evaluation comprises ADHD Rating Scale-Investigator Rated (ADHD-RS-IV) and/or the Conners' Adult Attention-Deficit/Hyperactivity Disorder Rating Scale-Self Report: Short Version (CAARS-S:S) and/or the Clinical Global Impression Scale (CGI)

BRIEF DESCRIPTION OF THE DRAWINGS

FIG. 2A shows that oral administration of PDC-1421 for 4 days significantly inhibits total activity of rats. And FIG. 2B exhibits that rearing of SHR rats is at the concentration of 675 mg/kg. Asterisk (*) represents P-value <0.05 between control and treatment groups. Double-asterisk (**)) represents P-value <0.01 between control and treatment groups.

DETAILED DESCRIPTION OF THE INVENTION

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

Example 1

Preparation of Radix Polygalae (*Polygala tenuifolia* Willd) Extract PDC-1421

Dry whole root of *P tenuifolia* Willd is cooked in water twice with a ratio of 100 kg to 800 kg under refluxing for one hour and a ratio of 100 kg to 700 kg under refluxing for another one hour. An aqueous extract is obtained after mixing the two cooked mixtures. The aqueous extract is concentrated to 400 kg by evaporation in vacuo and filtered by centrifugal filter. Then, the resulting concentrate is filtered by the resin column for chromatography. The specific filtering eluent is collected. The eluent is concentrated by evaporation in vacuo and dried by spray drier to yield a powder product PDC-1421.

Example 2

In Vivo Tetrabenazine-Induced Hypothermia Assay

Figure 1:
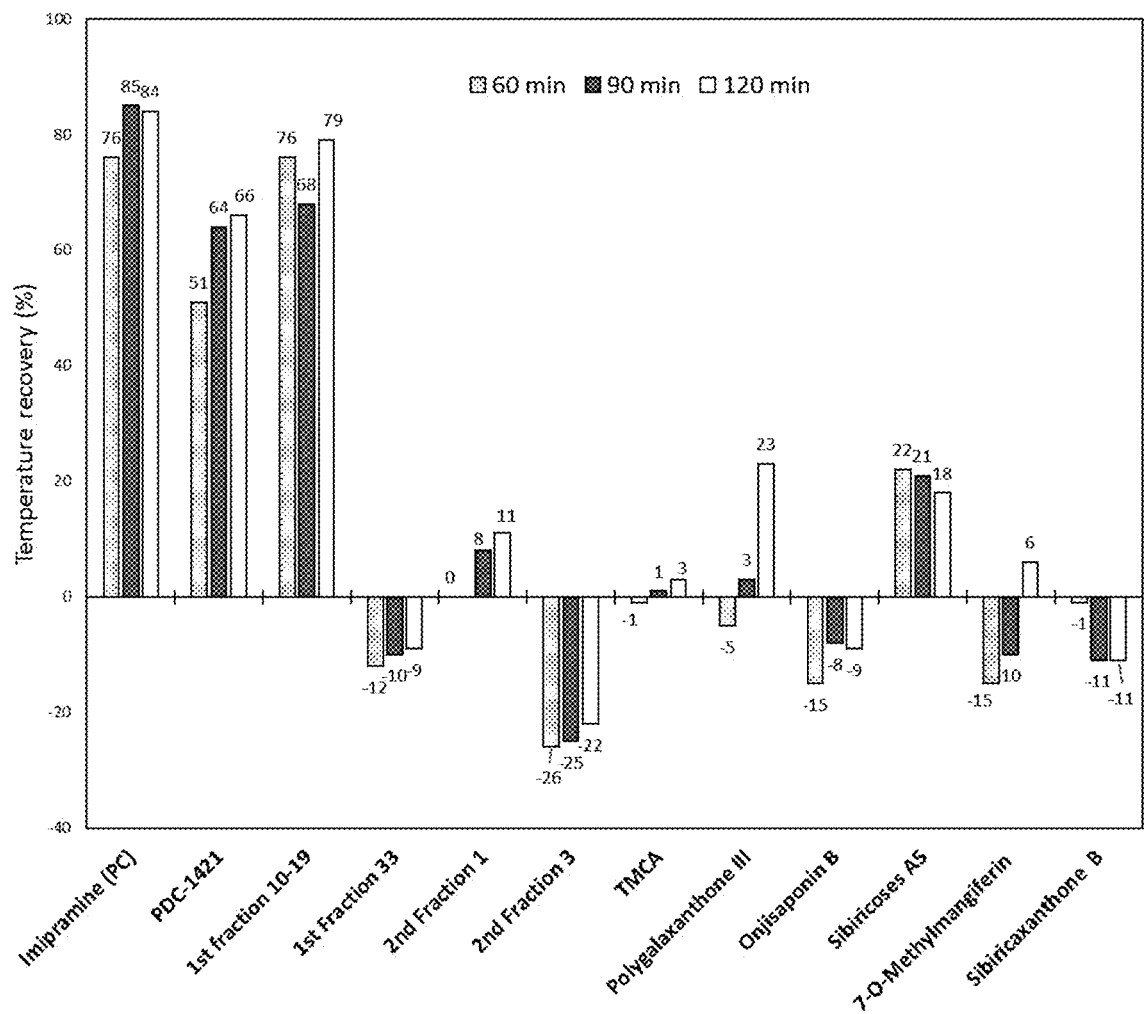
FIG. 1 depicts in vivo tetrabenazine-induced hypothermia test. Imipramine (positive control), PDC-1421, 1st Fraction 10-19, 1st Fraction 33, 2nd Fraction-1 (the major components are polygalatenosides AB/C), 2nd Fraction-3, TMCA, Polygalaxanthone III, Onjisaponin B, Sibiricose A5, 7-O-Methylmangiferin and Sibiricaxanthone B are administered as test substances and the temperature recovery (%) is documented as shown in figure.

The around 70% of PDC-1421 in Example 1 are composed of sucroester (34%), saponin (18%) and xanthone (17%). Some active compounds of in the powder product of Example 1, including polygalatenosides A/B/C (2nd fraction 1), ploygalaxanthone III, sibiricoses A5, and 7-O-methyl-mangiferin are also discovered through in vivo tetrabenazine-induced hypothermia test (one of rodent models for evaluating antidepressant-like activity in mice). Imipramine (as the positive control), PDC-1421, 1st Fraction 10-19, 1st Fraction 33, 2nd Fraction-1 (wherein the major components are polygalatenosides A/B/C), 2nd Fraction-3, TMCA, Polygalaxanthone III, Onjisaponin B, Sibiricose A5, 7-O-Methylmangiferin and Sibiricaxanthone B are dissolved in water for injection (WFI) and administered by oral gavage. The dosing volume is 10 mL/kg. Test substances and vehicle (WFI) are administered by oral gavage to groups of 8 ICR male mice weighing 23±3 g for 60 minutes, and then tetrabenazine (TBZ, 85 mg/kg) is injected intraperitoneally. Body temperature is recorded before (0 min), and 60, 90 and 120 min after TBZ challenge. The temperature recovery (%) of test substances is shown in the FIG. 1. Therefore, drug-induced hypothermia (e.g., TBZ and reserpine) animal model is a typical experiment to evaluate the activity of NRI on depression. Temperature recovery of TBZ-induced hypothermic response is considered as indication of a anti-depressant activity. FIG. 1 shows that the PDC-1421 and its fractions of "1st Fraction 33", "Polygalaxanthone III", "Sibiricoses A5" and "7-O-Methylmangiferin" had a temperature recovery at 120 min after TBZ challenge.

Example 3

In Vivo Attention Deficit/Hyperactivity Disorder Animal Model

The male spontaneously hypertensive rat (SHR) is orally given PDC-1421 of Example 1 dissolved in saline at a dosage of 75, 225 or 675 mg/kg bodyweight the negative control groups (Saline) are orally administered once a day for four days. A local motor activity assay is performed 60 minutes after administration on all animals at the first and the fourth day by recording horizontal activity of SHR within one hour in Automated Locomotor Activity Analysis System Chamber. Total activity, phase analysis, central/peripheral activity, and rearing are measured in local motor activity assay. Total activity is the most meaningful index for ADHD.

Figure 2A:
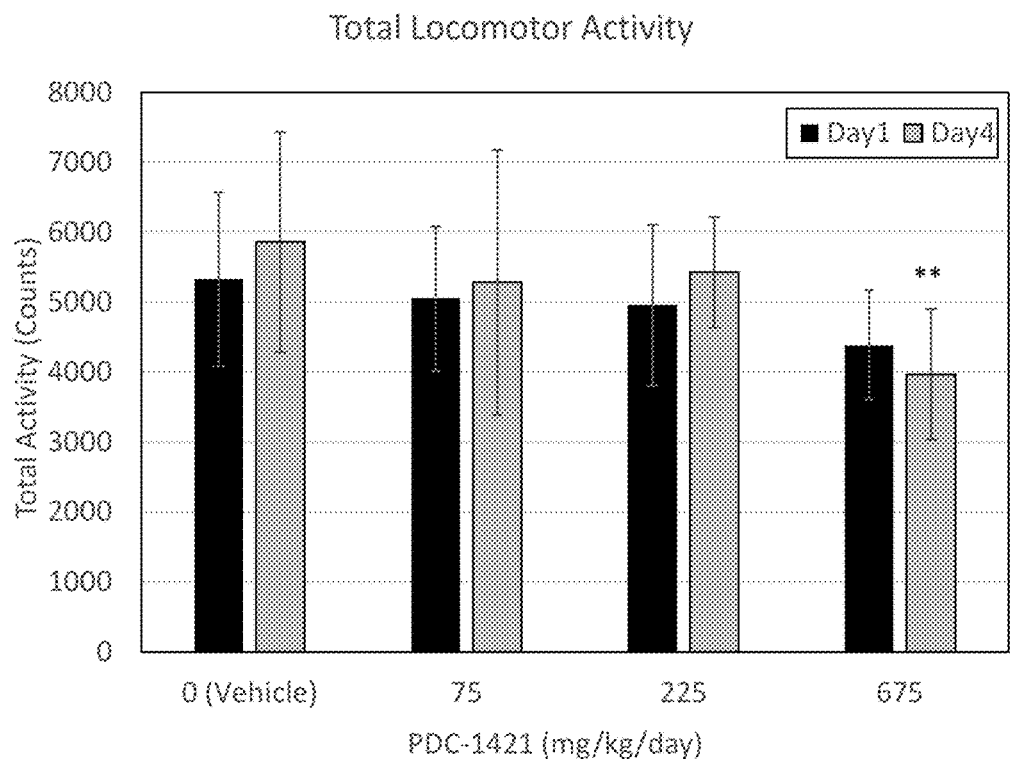
FIG. 2A-2B depict in vivo attention deficit/hyperactivity disorder animal model. Vehicle and PDC-1421 (75, 225, 675 mg/kg) are administered as test substances once a day for four days and the total activity (counts) is documented for analyzation.
Figure 2B:
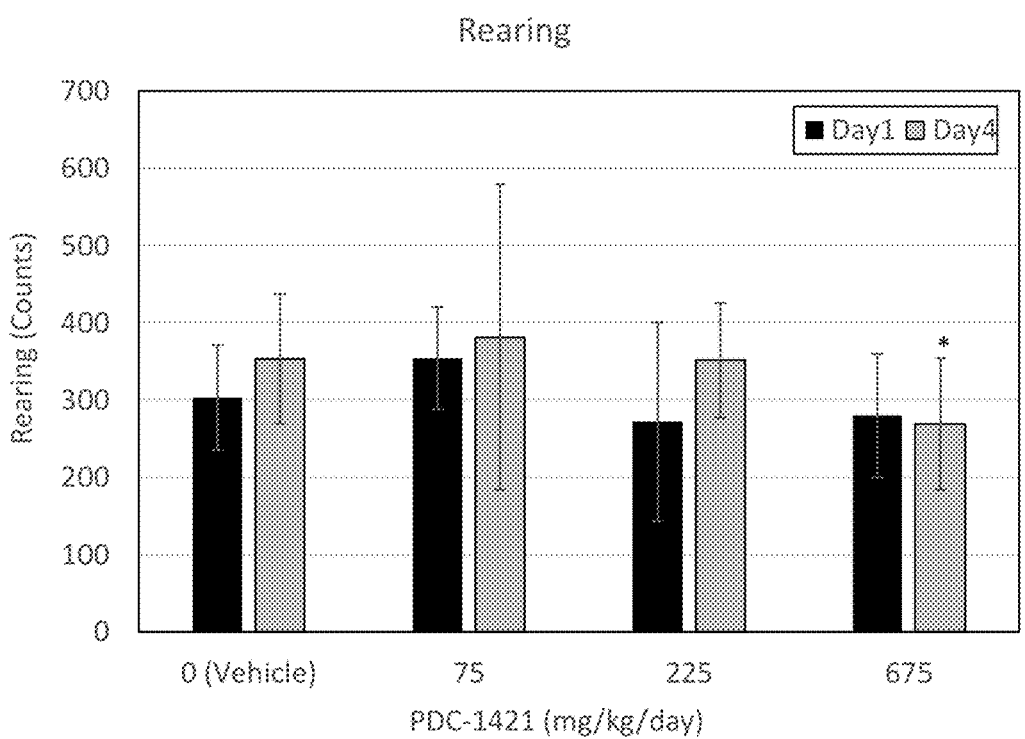

The results reveal that oral administration of PDC-1421 for 4 days significantly inhibits total activity and rearing of SHR rats at the concentration of 675 mg/kg, as shown in FIG. 2.

Example 4

Clinical Trial of Radix Polygalae (*Polygala tenuifolia* Willd) Extract PDC-1421

Preclinical Study for Recommended Dosage and Route of Administration

Based on the FDA's guidance documents, no observable adverse effect levels (NOAELs) from toxicity studies are used to estimate the starting dose. Table 2 summarizes the MRSD for 60 kg human/day calculated from the NOAEL of 28 day repeating dose studies in rats and in dogs using safety margin at 75-fold.

TABLE 1

Calculation of starting dose

| Study | Species | Dosage | HED | Dose for 60 kg human/day |
|---|---|---|---|---|
| 28-day repeated dose subacute oral toxicity study in rats | Rat | 3000 mg/kg (NOAEL) | 483.9 mg/kg | 387 mg/day (MRSD) |
| 28-day repeated dose subacute oral toxicity study in dogs | Dog | 3000 mg/kg (NOAEL) | 1666.7 mg/kg | 1333 mg/day (MRSD) |

NOAEL: No observable adverse effect level
HED: Human equivalent dose
MRSD: Maximum recommended starting dose
*The calculation of HED and MRSD are referred to FDA document.

Based on these calculations, the starting dose of PDC-1421 for human is 380 mg/day. In the proposed Phase I study, a single dose of PDC-1421 (oral administration) is used to evaluate the safety when taken by healthy subjects. The starting dose and dosage regimen are 380 mg PDC-1421 (one capsule of PDC-1421 Capsule) once a day after meal.

Preparation of PDC-1421 Capsule

A solid dosage form of a botanical extract of Radix Polygalae (*Polygala tenuifolia* Willd), such as PDC-1421, can be prepared into a gelatin capsule by conventional techniques known to those skilled in the art. In a preferred embodiment of the invention, the matrix comprises two excipients. The first excipient is silicon dioxide served as a glidant which may constitutes from about 2 to 10%, more preferably 5% of filling, and the second excipient is magnesium stearate served as a lubricant which may constitutes from about 2 to 10%, more preferably 5% of filling. The practical composition of PDC-1421 capsule for clinical trial is shown in Table 2.

TABLE 2

| Composition of PDC-1421 Capsule | | |
| --- | --- | --- |
| Name of Ingredient | Mg per Capsule | Function |
| PDC-1421 | 380 mg | Active ingredient |
| Silicon dioxide | 10 mg | Excipient |
| Magnesium stearate | 10 mg | Excipient |

Phase I Tested in Healthy Subject for Screening for Safety

In phase I trial, a total of 85 subjects are screened at study site and 30 subjects are enrolled. The 30 subjects are divided into four groups: 9 subjects in cohort A with 7 administered PDC-1421 (380 mg) and 2 administered placebo, 1 of 7 PDC-1421 subjects had no laboratory test data at baseline; 8 subjects in cohort B with 6 administered PDC-1421 (1140 mg) and 2 administered placebo; 4 subjects in cohort C with 3 administered PDC-1421 (2280 mg) and 1 administered placebo; and 9 subjects in cohort D with 7 administered PDC-1421 (3800 mg) and 2 administered placebo, 1 of 7 PDC-1421 subjects had abnormal laboratory data at screening visit.

Physical examination is determined to be "normal" on each body system in each cohort and no subject had dose-limiting toxicity (DLT) and toxicity grade.

All of the changes of vital signs from baseline of PDC-1421 and placebo group are mild and do not exceed the limit of normal range. Furthermore, all of the toxicity grades of vital signs are the lowest, systolic blood pressure in grade 1, increase >20 mm/Hg than baseline at 4 hours. No medical intervention/therapy is required. There is no correlation of changes from baseline or changes in the toxicity grade of vital signs between doses of PDC-1421. Only two grade 2 toxicity (at 24 hours in glucose in cohort A and at 4 hours in glucose in cohort B) occur in placebo group and no medical intervention/therapy were required for these cases Electrocardiogram (ECG) is determined to be "normal" in each time point and in each cohort. No subject had DLT and toxicity grade. Columbia-suicide severity rating scale (C-SSRS) are all 0 point on suicidal ideation, intensity of ideation, suicidal behavior in each cohort.

No subject has serious adverse event, and no subject is discontinued due to adverse event, and no clinically significant finding in physical examinations, vital signs, electrocardiogram, laboratory measurements, or C-SSRS is observed throughout the treatment period. The oral administration of PDC-1421 in healthy volunteers is safe and well-tolerated for the dose from 380 mg to 3800 mg. During the treatment period, 5 subjects are reported to experience 8 mild adverse events shown as Table 3. The severity of these 5 adverse events is all mild and no medical action required. There is no correlation of number, severity, relationship and outcome of adverse events found between doses of PDC-1421 and placebo. Further, there is no deviation of electrolyte level and no significant gastrointestinal discomfort during monitoring in the clinical trial. There are two mild adverse events such as lower heart rate and higher systolic blood pressure. Lower heart rate is that coupled to the dog telemetry study but not higher systolic blood pressure.

TABLE 3

| | Frequencies of Adverse Events | | | | |
| --- | --- | --- | --- | --- | --- |
| | Frequency | | | | |
| Adverse events BODY System | Cohort A (380 mg) N = 7 | Cohort B (1140 mg) N = 6 | Cohort C (2280 mg) N = 3 | Cohort D (3800 mg) N = 7 | Placebo N = 7 |
| Digest System | 3/7 | 0 | 0 | 0 | 1/7 |
| FLATULENCE | 2/7 | 0 | 0 | 0 | 1/7 |
| CONSTIPATION | 1/7 | 0 | 0 | 0 | 0 |
| Nervous System | 0 | 0 | 2/3 | 0 | 2/7 |
| SOMNOLENCE | 0 | 0 | 1/3 | 0 | 2/7 |
| STOMATITIS ULCER | 0 | 0 | 1/3 | 0 | 0 |

In summary, no subject has serious adverse event, and no subject is discontinued due to adverse event. No clinically significant findings in physical examinations, vital signs, electrocardiogram, laboratory measurements, and C-SSRS are observed throughout the treatment period. The oral administration of PDC-1421 in healthy volunteers is safe and well-tolerated for the dose from 380 mg to 3800 mg.

Phase II in Attention-Deficit Hyperactivity Disorder (ADHD) Patients

The Phase II clinical trial is aimed to evaluate the safety and efficacy of PDC-1421 in adults with ADHD. The study is a single center, open label, dose escalation evaluation with two dosage levels in six subjects. Six subjects are initially evaluated for safety and efficacy assessments at low-dose (1 capsule of PDC-1421, three times a day (TID)) for 28 days. The subjects who pass the safety checkpoint are further evaluated for safety and efficacy assessments at high-dose (2 capsules of PDC-1421 TID) for next 28 days.

The primary objective is to determine the efficacy profile of PDC-1421 capsule in ADHD with ADHD Rating Scale-IV (ADHD-RS-IV). The secondary objective is to evaluate the safety of PDC-1421 capsule in subjects receiving PDC-1421 at various dose levels.

A total of 6 subjects were enrolled in the study. All enrolled subjects received the low-dose of PDC-1421 capsules for 4 weeks, and all of the subjects received the high-dose of PDC-1421 capsules for next 4 weeks after passing the safety checkpoint. The safety population included 6 subjects, the intention-to-treat (ITT) population included 6 subjects, and the per protocol (PP) population included 5 subjects in the study. One subject was excluded from PP population due to drug compliance less than 80%.

Efficacy Results

For the primary endpoints, the percentages of improvement of 40% or greater in ADHD-RS-IV score from baseline to 8 weeks treatment are 83.3% (N=5) in the ITT population and 80.0% (N=4) in the PP population shown, as shown in Table 4. The net mean changes of ADHD-RS-IV scores from baseline to 8 weeks treatment are −25.7 in the ITT population and −24.6 in the PP population, as shown in Table 5.

TABLE 4

Summary of improvement ≥40% in inattention subscale (IA), hyperactivity-impulsivity (HI) and total subscale of ADHD-RS-IV from baseline up to 8 weeks treatment

| No. of subject, | ITT Population (N = 6) | | | PP Population (N = 5) | | |
| --- | --- | --- | --- | --- | --- | --- |
| n (%) | IA | HI | Total score | IA | HI | Total score |
| At Week 1 | 1 (16.7%) | 0 | 0 | 1 (16.7%) | 0 | 0 |
| At Week 2 | 1 (16.7%) | 3 (50.0%) | 1 (16.7%) | 1 (20.0%) | 3 (60.0%) | 1 (20.0%) |
| At Week 3 | 4 (66.7%) | 3 (50.0%) | 3 (50.0%) | 4 (80.0%) | 3 (60.0%) | 3 (60.0%) |
| At Week 4 | 3 (50.0%) | 3 (50.0%) | 3 (50.0%) | 3 (60.0%) | 3 (60.0%) | 3 (60.0%) |
| At Week 6 | 4 (66.7%) | 5 (83.3%) | 5 (83.3%) | 3 (60.0%) | 4 (80.0%) | 4 (80.0%) |
| At Week 8 | 4 (66.7%) | 6 (100.0%) | 5 (83.3%) | 3 (60.0%) | 5 (100.0%) | 4 (80.0%) |

TABLE 5

Summary of the inattention subscale, hyperactivity-impulsivity subscale and total scale raw score of ADHD-RS-IV

| ADHD-RS-IV | Total scale Mean (SD) | |
| --- | --- | --- |
| Treatment Period | ITT population (N = 6) | PP population (N = 5) |
| Week 0 (baseline) | 41.8 (6.6) | 40.2 (5.9) |
| Net change at Week 1 | −4.8 (6.0) | −5.2 (6.6) |
| Net change at Week 2 | −14.0 (7.9) | −15.2 (8.3) |
| Net change at Week 3 | −18.8 (10.0) | −20.2 (10.6) |
| Net change at Week 4 | −17.7 (13.2) | −20.4 (12.7) |
| Net change at Week 6 | −24.7 (10.0) | −22.8 (10.0) |
| Net change at Week 8 | −25.7 (11.0) | −24.6 (12.0) |

For the secondary endpoints, a statistically significant improvement in the ADHD index subscale and Impulsivity subscale of CAARS-S:S at Week 8 compared to baseline is occurred. The mean changes of CAARS-S:S from baseline to 8 weeks treatment for the ADHD index subscale and impulsivity subscale are −10.8 (P=0.0313) and −15.2 (P=0.0313) in the ITT population, and 10.6 (P=0.0625) and −14.0 (P=0.0625) in the PP population, as shown in Table 6. In addition, a significant improvement in ADHD index subscale is observed after 3 week low-dose PDC-1421 treatment (mean change=−8.7, P=0.0313). The T-scores of CAARS-S:S for other subscales including inattention/memory subscale, hyperactivity subscale and self-concept subscale, also show improvement at Week 8 compared to baseline, but no statistical significance.

TABLE 6

Summary of CAARS-S:S subscale T-score

| | CAARS-S:S | | | | |
|---|---|---|---|---|---|
| Treatment Period | Inattention/memory subscale Mean (SD) | Hyperactivity subscale Mean (SD) | Impulsivity subscale Mean (SD) | Self-concept subscale Mean (SD) | ADHD index subscale Mean (SD) |
| ITT population (N = 6) | | | | | |
| Week 0 (baseline) | 74.2 (7.9) | 65.2 (6.3) | 63.7 (10.2) | 65.0 (14.8) | 73.5 (8.3) |
| Net change at Week 1 | −1.5 (13.1) | 0.5 (4.4) | −4.5 (5.0) | −1.8 (3.3) | −2.3 (5.2) |
| Net change at Week 2 | −5.7 (9.0) | −0.2 (3.7) | −4.2 (6.5) | 1.7 (9.4) | −0.3 (5.9) |
| Net change at Week 3 | −12.2 (11.7) | −3.2 (8.4) | −11.2 (5.7)* | −4.0 (4.8) | −8.7 (6.1)* |
| Net change at Week 4 | −10.0 (10.2) | −6.2 (7.1) | −10.8 (7.1) | −5.7 (7.0) | −8.2 (7.4)* |
| Net change at Week 6 | −7.8 (12.7) | −5.2 (7.6) | −10.3 (10.9) | −3.3 (5.4) | −8.0 (5.5)* |
| Net change at Week 8 | −10.5 (11.0) | −5.2 (5.9) | −15.2 (7.9)* | −4.7 (6.2) | −10.8 (6.2)* |
| PP population (N = 5) | | | | | |
| Week 0 (baseline) | 72.2 (7.0) | 63.4 (5.1) | 60.8 (8.2) | 60.2 (10.1) | 70.2 (2.0) |
| Net change at Week 1 | −1.2 (14.7) | 1.2 (4.5) | −3.2 (4.3) | −2.2 (3.5) | −2.8 (5.7) |
| Net change at Week 2 | −6.2 (10.0) | −0.2 (4.1) | −2.8 (6.2) | 2.0 (10.5) | −0.2 (6.5) |
| Net change at Week 3 | −11.8 (13.1) | −3.8 (9.3) | −11.2 (6.4) | −4.8 (4.9) | −9.8 (6.1) |
| Net change at Week 4 | −11.4 (10.7) | −7.4 (7.2) | −10.2 (7.8) | −6.8 (7.2) | −9.6 (7.2) |
| Net change at Week 6 | −6.6 (13.8) | −5.6 (8.4) | −9.6 (12.0) | −3.2 (6.1) | −7.8 (6.2) |
| Net change at Week 8 | −10.6 (12.3) | −5.6 (6.5) | −14.0 (8.2) | −4.8 (6.9) | −10.6 (6.9) |

*p-value < 0.05

For the both ITT and PP populations, the percentages of CGI-ADHD-Improvement score less than or equal to 2 at Week 8 are 100% (N=6 for ITT, N=5 for PP), as shown in Table 7. For ITT population, the mean scores of CGI-ADHD-S at baseline and Week 8 are 5.3 (SD=0.5) and 2.7 (SD=1.0) respectively. The net mean changes of CGI-ADHD-Severity score from base line to Week 8 is 2.6 points.

TABLE 7

Summary of clinical global impression scale (CGI) score of 2 or Lower

| | CGI | | | |
|---|---|---|---|---|
| | ITT Population (N = 6) | | PP Population (N = 5) | |
| Treatment Period | CGI-ADHD-Severity of illness | CGI-ADHD-Improvement | CGI-ADHD-Severity of illness | CGI-ADHD-Improvement |
| | CGI score, mean (SD) | | | |
| At Week 0 (baseline) | 5.3 (0.5) | — | 5.2 (0.4) | — |
| At Week 1 | 5.0 (0.9) | 3.7 (0.5) | 4.8 (0.8) | 3.6 (0.5) |
| At Week 2 | 4.3 (0.5) | 2.8 (0.4) | 4.2 (0.4) | 2.8 (0.4) |
| At Week 3 | 3.7 (0.8) | 2.7 (0.5) | 3.4 (0.5) | 2.6 (0.5) |
| At Week 4 | 4.0 (0.9) | 3.0 (0.6) | 3.8 (0.8) | 3.0 (0.7) |
| At Week 6 | 3.3 (0.5) | 2.2 (0.8) | 3.4 (0.5) | 2.2 (0.8) |
| At Week 8 | 2.7 (1.0) | 1.5 (0.5) | 2.4 (0.9) | 1.4 (0.5) |

TABLE 7-continued

Summary of clinical global impression scale (CGI) score of 2 or Lower

| | CGI | | | |
|---|---|---|---|---|
| | ITT Population (N = 6) | | PP Population (N = 5) | |
| Treatment Period | CGI-ADHD-Severity of illness | CGI-ADHD-Improvement | CGI-ADHD-Severity of illness | CGI-ADHD-Improvement |
| | No. of subject of CGI score of 2 or Lower, n (%) | | | |
| At Week 1 | 0 (0.0%) | 0 (0.0%) | 0 (0.0%) | 0 (0.0%) |
| At Week 2 | 0 (0.0%) | 1 (16.7%) | 0 (0.0%) | 1 (20.0%) |
| At Week 3 | 0 (0.0%) | 2 (33.3%) | 0 (0.0%) | 2 (4.0%) |
| At Week 4 | 0 (0.0%) | 1 (16.7%) | 0 (0.0%) | 1 (20.0%) |
| At Week 6 | 0 (0.0%) | 4 (66.7%) | 0 (0.0%) | 3 (60.0%) |
| At Week 8 | 2 (33.3%) | 6 (100.0%) | 3 (60.0%) | 5 (100.0%) |

Safety Results

The safety evaluation is based on the ITT population, who takes at least one dose of the IPs and has any of the post-baseline safety data collected.

Regarding the incidence of adverse events (AEs), a total 4 subjects (66.7%) experience at least one AE and a total of 23 AEs are observed duration of the study. No subjects withdraw from the study due to AE.

For more common AEs, the most frequently reported AEs in the study include "Gastrointestinal disorders" (Overall: N=3 [50.0%]; Unlikely: N=1; Possibly: N=2) and "Respiratory, thoracic and mediastinal disorders" (Overall: N=3 [50.0%]; Unrelated: N=3).

There are no life-threatening AEs and deaths. For level of severity, the grade of most AEs is moderate (N=13). There are 1 case of severe AE and 9 cases of mild AEs. One event ("Dizziness") rated as severe is judged as "Possibly" to study drug by the investigator.

Regarding the laboratory values at each scheduled visit, few abnormal values without clinically significant are observed. The results suggest that treatment of PDC-1421 did not increase the abnormalities of laboratory data.

For vital signs and electrocardiogram (ECG), no abnormal body temperature and ECG are observed and some abnormal blood pressure and heart rate without clinically significant are observed in the study. The results suggest that treatment of PDC-1421 does not increase the abnormalities of vital signs.

For physical examination, no subjects are evaluated as abnormal for all the scheduled visits (Visit 1 and Visit 8) in the study. No physical evaluation becomes worse during treatment and follow-up period.

For C-SSRS evaluation, no suicide-related treatment-emergent event occurs in the study. The results suggest that treatment of PDC-1421 does not increase the risk of either suicidal ideation or suicidal behavior.

In summary, the present invention provides a method of treating ADHD in a safer and more effective way by administering a composition comprising a Radix Polygalae extract. In clinical trial, the subjects given the treatment of the composition have significant improvements in many ADHD related scale evaluations. And compared with the current medications for ADHD, the method of present shows no side effects on cardiovascular system or mental state. It is showed in all cases that the method of the present invention is a better treatment for ADHD and relatively safe.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating attention-deficit/hyperactivity disorder (ADHD) a method of treating attention-deficit/hyperactivity disorder (ADHD), comprising administering a composition comprising an effective amount of a botanical extract to a subject in need thereof, wherein the botanical extraction is one or a combination of:
    (i) a polar solvent extract from the dry root of *Polygala tenuifolia* Willd, wherein the polar solvent is water, a mixture of water and methanol, or a mixture of water and ethanol;
    (ii) (ii) an aqueous fraction resulting from an organic solvent extraction of the polar solvent extract of (i);
    (iii) (iii) an organic eluent obtained by introducing the polar solvent extract of (i) or the aqueous fraction of (ii) into a reverse phase chromatography column, and eluting the column with water and an organic solvent; and
    (iv) (iv) a filtrate of the organic eluent (iii) having a molecular mass less than 30,000 Dalton,
    wherein the composition is administered in a capsule comprising 380 mg of the *Polygala tenuifolia* Willd extract with a daily dose of 380-3800 mg.

2. The method of claim 1, wherein the composition further comprises silicon dioxide and magnesium stearate as excipients.

3. The method of claim 1, wherein the composition is administered at an onset of an episode of a symptom of ADHD.

4. The method of claim 3, wherein the symptom comprises inattention, memory problems, hyperactivity, impulsivity and problem with self-concept.

* * * * *